US009289290B2

(12) United States Patent
Alkhatib et al.

(10) Patent No.: US 9,289,290 B2
(45) Date of Patent: *Mar. 22, 2016

(54) COLLAPSIBLE/EXPANDABLE PROSTHETIC HEART VALVES WITH NATIVE CALCIFIED LEAFLET RETENTION FEATURES (71) Applicant: St. Jude Medical, Inc., St. Paul, MN (US)

(72) Inventors: Yousef F. Alkhatib, Edina, MN (US); Michael J. Girard, Lino Lakes, MN (US)

(73) Assignee: St. Jude Medical, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/280,868

(22) Filed: May 19, 2014

(65) Prior Publication Data
US 2014/0303723 A1 Oct. 9, 2014

Related U.S. Application Data (63) Continuation of application No. 12/733,763, filed as application No. PCT/US2008/011181 on Sep. 26, 2008, now Pat. No. 8,784,481.

(60) Provisional application No. 60/995,845, filed on Sep. 28, 2007.

(51) Int. Cl.
*A61F 2/24* (2006.01)
(52) U.S. Cl.
CPC .............. *A61F 2/2412* (2013.01); *A61F 2/2418* (2013.01); *A61F 2230/0054* (2013.01); *A61F 2230/0076* (2013.01)

(58) Field of Classification Search
CPC ........................................................ A61F 2/24
USPC .................................................. 623/2.1–2.19
See application file for complete search history.

(56) References Cited

U.S. PATENT DOCUMENTS

| 3,657,744 | A | 4/1972 | Ersek |
| 4,192,020 | A | 3/1980 | Davis et al. |
| 4,275,469 | A | 6/1981 | Gabbay |

(Continued)

FOREIGN PATENT DOCUMENTS

| DE | 19857887 A1 | 7/2000 |
| DE | 10121210 A1 | 11/2002 |

(Continued)

OTHER PUBLICATIONS

International Search Report for Application No. PCT/US2008/011181 dated Feb. 18, 2009.

(Continued)

*Primary Examiner* — Suzette J Gherbi
(74) *Attorney, Agent, or Firm* — Lerner, David, Littenberg, Krumholz & Mentlik, LLP (57) ABSTRACT A prosthetic heart valve is circumferentially collapsible for less invasive delivery into a patient. The valve re-expands to operating size at the implant site in the patient. A frame structure of the valve includes restraining structure that can help to push one or more of the patient's native heart valve leaflets radially outwardly so that this native leaflet tissue does not interfere with the operation or service life of the prosthetic valve.

20 Claims, 8 Drawing Sheets

(56) References Cited

U.S. PATENT DOCUMENTS

| | | |
|---|---|---|
| 4,340,091 A | 7/1982 | Skelton et al. |
| 4,423,730 A | 1/1984 | Gabbay |
| 4,491,986 A | 1/1985 | Gabbay |
| 4,731,074 A | 3/1988 | Rousseau et al. |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |
| 5,843,167 A | 12/1998 | Dwyer et al. |
| 5,855,601 A | 1/1999 | Bessler et al. |
| 5,924,424 A | 7/1999 | Stevens et al. |
| 5,935,163 A | 8/1999 | Gabbay |
| 5,961,549 A | 10/1999 | Nguyen et al. |
| 5,968,068 A | 10/1999 | Dehdashtian et al. |
| 6,077,297 A | 6/2000 | Robinson et al. |
| 6,083,257 A | 7/2000 | Taylor et al. |
| 6,090,140 A | 7/2000 | Gabbay |
| 6,168,614 B1 | 1/2001 | Andersen et al. |
| 6,214,036 B1 | 4/2001 | Letendre et al. |
| 6,264,691 B1 | 7/2001 | Gabbay |
| 6,267,783 B1 | 7/2001 | Letendre et al. |
| 6,306,141 B1 | 10/2001 | Jervis |
| 6,312,465 B1 | 11/2001 | Griffin et al. |
| 6,358,277 B1 | 3/2002 | Duran |
| 6,368,348 B1 | 4/2002 | Gabbay |
| 6,419,695 B1 | 7/2002 | Gabbay |
| 6,425,916 B1 | 7/2002 | Garrison et al. |
| 6,454,799 B1 | 9/2002 | Schreck |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,726,715 B2 | 4/2004 | Sutherland |
| 6,730,118 B2 | 5/2004 | Spenser et al. |
| 6,733,525 B2 | 5/2004 | Yang et al. |
| 6,767,362 B2 | 7/2004 | Schreck |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,830,585 B1 | 12/2004 | Artof et al. |
| 6,869,444 B2 | 3/2005 | Gabbay |
| 6,875,231 B2 | 4/2005 | Anduiza et al. |
| 6,893,460 B2 | 5/2005 | Spenser et al. |
| 6,908,481 B2 | 6/2005 | Cribier |
| 6,916,338 B2 | 7/2005 | Speziali |
| 7,018,406 B2 | 3/2006 | Seguin et al. |
| 7,025,780 B2 | 4/2006 | Gabbay |
| 7,041,132 B2 | 5/2006 | Quijano et al. |
| 7,044,966 B2 | 5/2006 | Svanidze et al. |
| 7,101,396 B2 | 9/2006 | Artof et al. |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,329,278 B2 | 2/2008 | Seguin et al. |
| 7,331,993 B2 | 2/2008 | White |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,871,436 B2 | 1/2011 | Ryan et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 8,444,689 B2 | 5/2013 | Zhang |
| D684,692 S | 6/2013 | Braido |
| 8,454,686 B2 | 6/2013 | Alkhatib |
| 8,465,540 B2 | 6/2013 | Straubinger et al. |
| 8,597,349 B2 | 12/2013 | Alkhatib |
| 8,728,154 B2 | 5/2014 | Alkhatib |
| 8,784,481 B2 * | 7/2014 | Alkhatib et al. ............. 623/2.18 |
| 8,808,366 B2 * | 8/2014 | Braido et al. ................. 623/2.1 |
| 8,882,831 B2 | 11/2014 | Alkhatib |
| 8,961,595 B2 | 2/2015 | Alkhatib |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0055495 A1 | 3/2003 | Pease et al. |
| 2003/0055496 A1 | 3/2003 | Cai et al. |
| 2003/0130726 A1 | 7/2003 | Thorpe et al. |
| 2003/0153974 A1 | 8/2003 | Spenser et al. |
| 2003/0153975 A1 | 8/2003 | Byrd et al. |
| 2004/0039436 A1 | 2/2004 | Spenser et al. |
| 2004/0049262 A1 | 3/2004 | Obermiller et al. |
| 2004/0088046 A1 | 5/2004 | Speziali |
| 2004/0093060 A1 | 5/2004 | Seguin et al. |
| 2004/0093075 A1 | 5/2004 | Kuehne |
| 2004/0186563 A1 | 9/2004 | Lobbi |
| 2004/0186565 A1 | 9/2004 | Schreck |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0177227 A1 | 8/2005 | Heim et al. |
| 2005/0192665 A1 | 9/2005 | Spenser et al. |
| 2005/0197695 A1 | 9/2005 | Stacchino et al. |
| 2005/0209689 A1 | 9/2005 | Speziali |
| 2005/0256566 A1 | 11/2005 | Gabbay |
| 2006/0008497 A1 | 1/2006 | Gabbay |
| 2006/0074484 A1 | 4/2006 | Huber |
| 2006/0106415 A1 | 5/2006 | Gabbay |
| 2006/0122692 A1 | 6/2006 | Gilad et al. |
| 2006/0142848 A1 | 6/2006 | Gabbay |
| 2006/0149360 A1 | 7/2006 | Schwammenthal et al. |
| 2006/0167468 A1 | 7/2006 | Gabbay |
| 2006/0173532 A1 | 8/2006 | Flagle et al. |
| 2006/0178740 A1 | 8/2006 | Stacchino et al. |
| 2006/0190074 A1 | 8/2006 | Hill et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073391 A1 | 3/2007 | Bourang et al. |
| 2007/0088431 A1 | 4/2007 | Bourang et al. |
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0118210 A1 | 5/2007 | Pinchuk |
| 2007/0162100 A1 | 7/2007 | Gabbay |

(56) References Cited

U.S. PATENT DOCUMENTS

| | | |
|---|---|---|
| 2007/0168013 A1 | 7/2007 | Douglas |
| 2007/0203575 A1 | 8/2007 | Forster et al. |
| 2007/0213813 A1 | 9/2007 | Von Segesser et al. |
| 2007/0233228 A1 | 10/2007 | Eberhardt et al. |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0282436 A1 | 12/2007 | Pinchuk |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071368 A1 | 3/2008 | Tuval et al. |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147179 A1 | 6/2008 | Cai et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0228263 A1 | 9/2008 | Ryan |
| 2008/0228264 A1 | 9/2008 | Li et al. |
| 2008/0243245 A1 | 10/2008 | Thambar et al. |
| 2008/0243246 A1 | 10/2008 | Ryan et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0054975 A1 | 2/2009 | del Nido et al. |
| 2009/0112309 A1 | 4/2009 | Jaramillo et al. |
| 2009/0138079 A1 | 5/2009 | Tuval et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0114307 A1 | 5/2010 | Agnew et al. |
| 2010/0131054 A1 | 5/2010 | Tuval et al. |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0082539 A1 | 4/2011 | Suri |
| 2011/0224678 A1 | 9/2011 | Gabbay |
| 2012/0078347 A1* | 3/2012 | Braido et al. ............ 623/1.26 |
| 2014/0296966 A1* | 10/2014 | Braido et al. ............ 623/1.26 |

FOREIGN PATENT DOCUMENTS

| | | |
|---|---|---|
| DE | 202008009610 U1 | 12/2008 |
| EP | 0331345 A2 | 9/1989 |
| EP | 0850607 A1 | 7/1998 |
| EP | 1000590 A1 | 5/2000 |
| EP | 1129744 A1 | 9/2001 |
| EP | 1157673 A2 | 11/2001 |
| EP | 1360942 A1 | 11/2003 |
| EP | 1584306 A1 | 10/2005 |
| EP | 1598031 A2 | 11/2005 |
| EP | 1926455 A2 | 6/2008 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2004047619 A2 | 6/2004 |
| WO | 2006073626 A2 | 7/2006 |
| WO | 2007013999 A2 | 2/2007 |
| WO | 2007053243 A2 | 5/2007 |
| WO | 2007071436 A2 | 6/2007 |
| WO | 2008070797 A2 | 6/2008 |
| WO | 2009029199 A1 | 3/2009 |
| WO | 2009042196 A2 | 4/2009 |
| WO | 2009045332 A2 | 4/2009 |
| WO | 2009045334 A1 | 4/2009 |
| WO | 2010008548 A2 | 1/2010 |
| WO | 2010008549 A1 | 1/2010 |
| WO | 2010051025 A1 | 5/2010 |
| WO | 2010087975 A1 | 8/2010 |
| WO | 2010096176 A1 | 8/2010 |
| WO | 2010098857 A1 | 9/2010 |
| WO | 2013075215 A1 | 5/2013 |

OTHER PUBLICATIONS

PCT International Search Report date Jan. 26, 2009.
U.S. Appl. No. 29/375,232.
U.S. Appl. No. 29/375,235.
U.S. Appl. No. 29/375,238.
U.S. Appl. No. 29/375,239.
U.S. Appl. No. 29/375,243.
U.S. Appl. No. 29/375,245.
U.S. Appl. No. 29/375,251.
U.S. Appl. No. 29/375,252.
U.S. Appl. No. 29/375,253.
U.S. Appl. No. 29/375,254.
U.S. Appl. No. 29/375,257.
U.S. Appl. No. 29/375,258.
U.S. Appl. No. 29/375,260.
Andersen, Henning Rud, Transluminal Catheter Implanted Prosthetic Heart Valves, International Journal of Angiology 7:102-106 (1998).
Catheter-implanted prosthetic heart valves, Knudsen, L.L., et al., The International Journal of Artificial Organs, vol. 16, No. 5 1993, pp. 253-262.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Quaden, Renéet al., "Percutaneous aortic valve replacement: resection before implantation," 836-840, European J. of Cardio-thoracic Surgery 27 (2005).
Ruiz, Carlos, "Overview of PRE-CE Mark Transcatheter Aortic Valve Technologies", Euro PCR, May 25, 2010.
Transluminal Aortic Valve Placement, Moazami, Nader, et al., ASAIO Journal, 1996; 42:M381-M385.
Transluminal implantation of artificial heart valves, Andersen, H. R., et al., European Heart Journal (1992) 13, 704-708.
Zegdi, Rachid, MD, PhD et al., "Is It Reasonable to Treat All Calcified Stenotic Aortic Valves With a Valved Stent?" 579-584, J. of the American College of Cardiology, vol. 51, No. 5, Feb. 5, 2008.

* cited by examiner

COLLAPSIBLE/EXPANDABLE PROSTHETIC HEART VALVES WITH NATIVE CALCIFIED LEAFLET RETENTION FEATURES

CROSS REFERENCES TO RELATED APPLICATIONS

The present application is a continuation of U.S. patent application Ser. No. 12/733,763, filed Mar. 18, 2010, which is a national phase entry under 35 U.S.C. §371 of International Application No. PCT/US2008/011181, filed Sep. 26, 2008, published on Apr. 9, 2009 as WO 2009/045334, which claims the benefit of U.S. provisional patent application No. 60/995,845, filed Sep. 28, 2007, which are hereby incorporated by reference herein in their entireties.

BACKGROUND OF THE INVENTION

This invention relates to collapsible/expandable prosthetic heart valves (especially prosthetic aortic valves) for use with non-resected calcified native valves. The prosthetic heart valve design incorporates features that hold open the native calcified leaflets away from the new valve.

SUMMARY OF THE INVENTION

In accordance with certain possible aspects of the invention, a prosthetic heart valve may utilize expansion of fork-like fingers to push calcified native leaflets out of the way. This eliminates interference with the newly deployed prosthetic valve and maximizes hemodynamic performance. It also enhances prosthetic valve frame anchoring in the patient as a result of the fingers engaging the calcified leaflets.

A prosthetic heart valve in accordance with the invention may be circumferentially collapsible and re-expandable, and may include an annular frame structure and a flexible leaflet structure disposed in the frame structure. The frame structure is preferably adapted for delivery into a patient's native heart valve annulus in a circumferentially collapsed condition. The frame structure is preferably further adapted for circumferential re-expansion when in the above-mentioned annulus. The frame structure preferably includes a leaflet restraining structure for pushing radially outwardly on a patient's native heart valve leaflet (or leaflets) when the frame structure is re-expanded. The leaflet restraining structure is preferably cantilevered from an annulus portion of the frame structure. (The annulus portion is the portion of the frame structure that re-expands in the native valve annulus.) More particularly, the leaflet restraining structure is preferably cantilevered from the annulus portion to a free end of the leaflet restraining structure that is downstream from the annulus portion in the direction of blood flow through the prosthetic valve when the prosthetic valve is in use in the patient.

The above-mentioned leaflet restraining structure may be resiliently biased to incline radially outwardly from the annulus portion as one proceeds along the restraining structure from the annulus portion toward the free end of the restraining structure.

The leaflet restraining structure may include a plurality of fingers that are spaced from one another in a direction that is circumferential around the annulus portion. Each of these fingers may be cantilevered from the annulus portion and may extend from the annulus portion in the direction of blood flow through the implanted prosthetic valve.

Each of the above-mentioned fingers may have a free end that is remote from the annulus portion. All of the fingers may extend to approximately the same distance downstream from the annulus portion in the direction of blood flow. Alternatively, a first of the fingers may extend a greater distance downstream from the annulus portion in the direction of blood flow than a second of the fingers.

The annulus portion may include two (or more) circumferentially spaced commissure regions. In such a case, and in the case of the alternative mentioned in the immediately preceding paragraph, the fingers may also be circumferentially spaced from one another between two of the commissure regions, and the above-mentioned first finger may be circumferentially closer to one of the above-mentioned two commissure regions than the above-mentioned second finger is to either of those two commissure regions.

In a case in which the leaflet restraining structure includes a plurality of fingers, the leaflet restraining structure may further include a linking structure between two circumferentially adjacent ones of the fingers. This linking structure may be downstream from the annulus portion in the direction of blood flow through the implanted prosthetic valve.

The immediately above-mentioned linking structure may be collapsible and re-expandable in a direction that is circumferential around the annulus portion.

The location of the above-mentioned linking structure may be at the ends of the linked fingers that are remote from the annulus portion.

The annulus portion may include a plurality of circumferentially spaced commissure regions, and the leaflet restraining structure may be circumferentially spaced between two circumferentially adjacent ones of those commissure regions. Especially in such a case, the leaflet restraining structure may be one of a plurality of similar leaflet restraining structures. Each of these leaflet restraining structures may be circumferentially spaced between a respective one of a plurality of pairs of circumferentially adjacent ones of the commissure regions.

The prosthetic heart valve may be an aortic valve, which may further comprise a further frame structure that includes an annular aortic portion and a plurality of struts or links between the aortic portion and the annulus portion. The aortic portion may be adapted for delivery into a patient's aorta in a circumferentially collapsed condition. The aortic portion may be further adapted to circumferentially re-expand when in the aorta. The aortic portion is preferably downstream from the free end of the leaflet restraining structure in the direction of blood flow. The above-mentioned struts or links are preferably circumferentially spaced from the leaflet restraining structure.

In cases like those mentioned in the immediately preceding paragraph, the annulus portion may include a plurality of circumferentially spaced commissure regions. The above-mentioned struts or links may then connect to the annulus portion adjacent the commissure regions. For example, the leaflet restraining structure may be circumferentially spaced between first and second circumferentially adjacent ones of the links, and the first and second links may be respectively connected to the annulus portion adjacent respective first and second circumferentially adjacent ones of the commissure regions.

Further features of the invention, its nature and various advantages, will be more apparent from the accompanying drawings and the following detailed description.

BRIEF DESCRIPTION OF THE DRAWINGS

FIG. 3a is a simplified view of an illustrative embodiment of a prosthetic heart valve component in accordance with the invention. FIG. 3a shows the depicted component as though cut along a vertical axis and then laid out flat.

DETAILED DESCRIPTION

A collapsible and re-expandable prosthetic aortic valve that can self-anchor around the native commissures in the valsalva sinus is shown in Alkhatib PCT patent application Ser. No. PCT/US08/09950, filed Aug. 21, 2008, which is hereby incorporated by reference herein in its entirety. The illustrations that form part of the present disclosure are embodiments of valves like those shown in the above-mentioned reference, with the addition of leaflet retention or restraining features in accordance with this invention. It will be understood that the particular structures shown and described herein are only illustrative, and that the invention can be applied to many other prosthetic valve constructions. Some of these possible variations will be mentioned later in this specification.

FIGS. 1a-d are several views of an illustrative embodiment of the invention, including fork-like fingers 10 for pushing a patient's native leaflet tissue (which may be calcified) out of the way of the leaflet structure 20 of prosthetic heart valve 30. The upper free ends of fingers 10 are cantilevered from annular stent structure 40 of the valve. When the valve is implanted in a patient, stent structure 40 resides in or near the patient's native valve annulus. Hence this portion 40 of the frame structure of valve 30 may sometimes be referred to as the annulus portion of the frame structure. Valve 30 is configured for use as an aortic valve replacement. In such use, an annular aortic portion 50 of the valve resides in the patient's aorta downstream (in the direction of blood flow through the implanted valve) from the patient's native valve annulus. Portions 40 and 50 are connected to one another by a plurality of links or struts 60 that pass through the patient's native valsalva sinus and that bulge out into the outwardly bulging lobes of the valsalva sinus. Other details of the construction of valve 30 will more apparent from the above-mentioned Alkhatib reference.

Note that all of the valves shown herein may be elastically collapsible in the annular or circumferential direction to a reduced annular or circumferential size that is suitable for delivery into a patient in a less invasive way (e.g., through tube-like delivery apparatus such as a catheter, a trocar, a laparoscopic instrument, or the like). When the valve reaches the intended site for implantation, the valve may elastically re-expand to normal operating size (e.g., the size shown in FIGS. 1a-d). In all cases herein, the valve frame structure like 10/40/50/60 may be made of a highly elastic metal such as nitinol, while leaflet structure 20 may be made of a synthetic material such as polymer, a natural material such as tissue, or another suitable flexible material. In addition to the structural elements shown herein, valves in accordance with this invention may also include other elements such as other layers of tissue and/or fabric (e.g., an outer fabric cover).

Figure 1A:
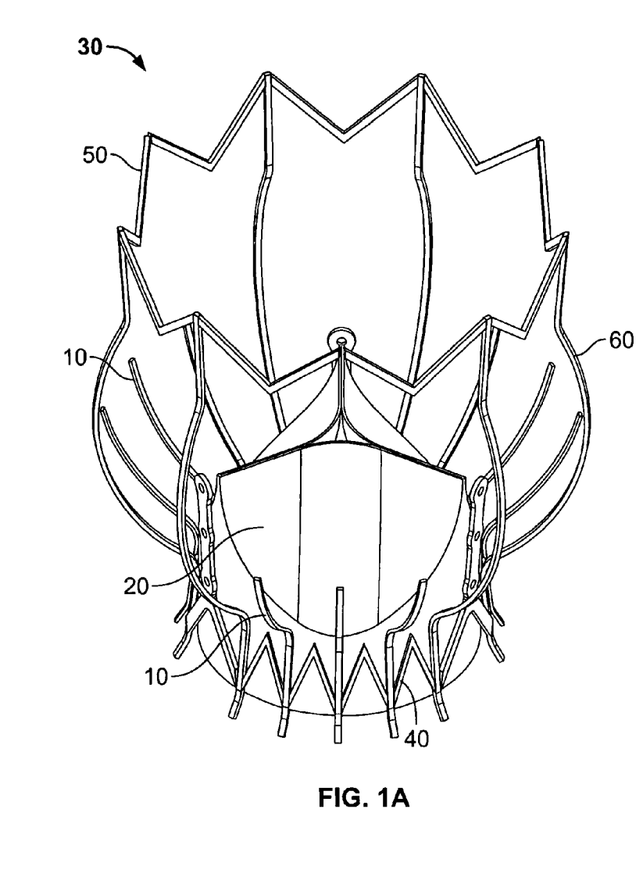
FIG. 1a is a simplified isometric or perspective view of an illustrative embodiment of a prosthetic heart valve in accordance with the invention.
Figure 1B:
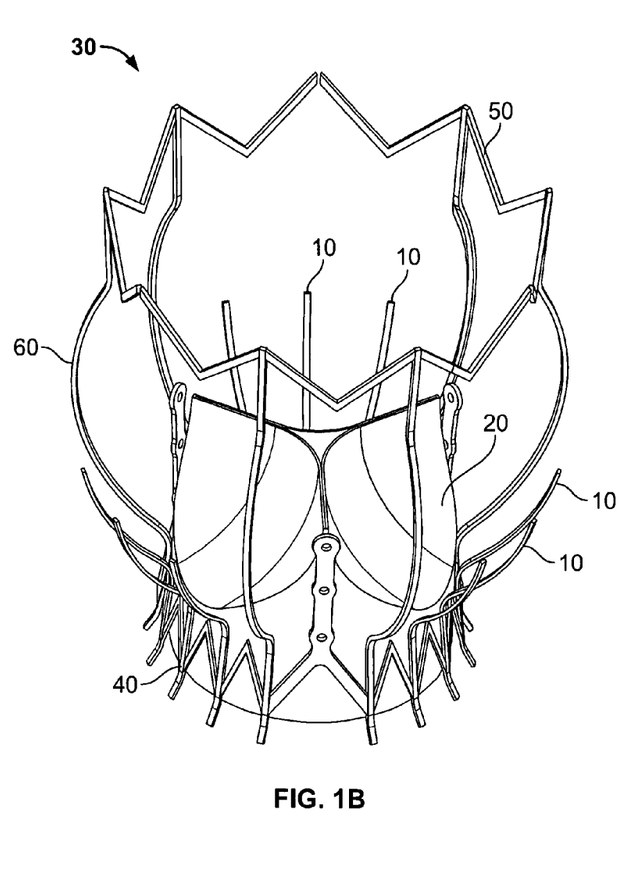
FIG. 1b shows the FIG. 1a structure from another angle.
Figure 1C:
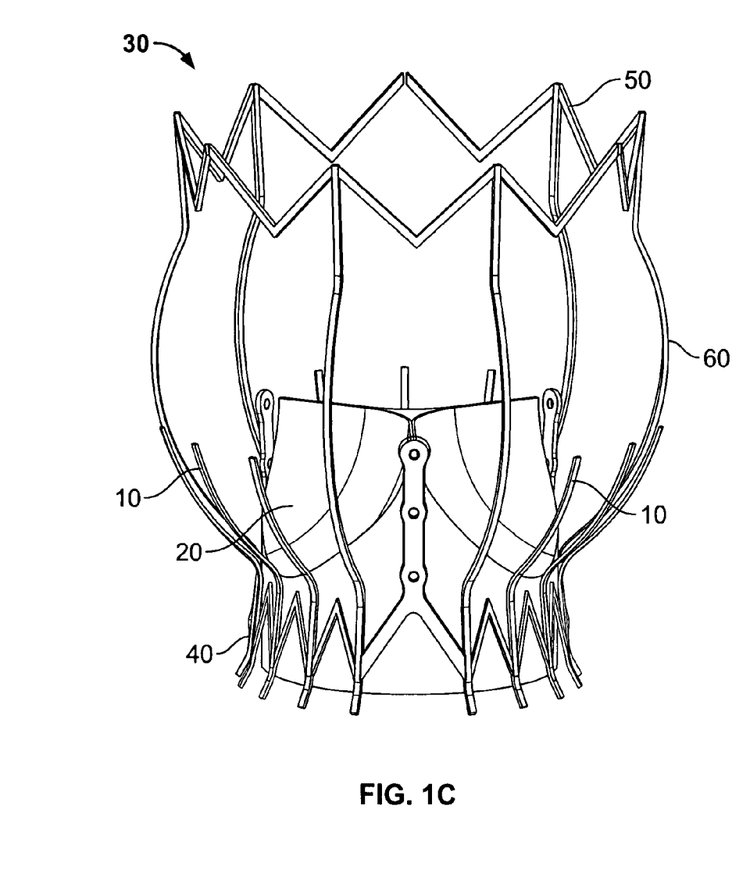
FIG. 1c shows the FIG. 1b structure from yet another angle.
Figure 1D:
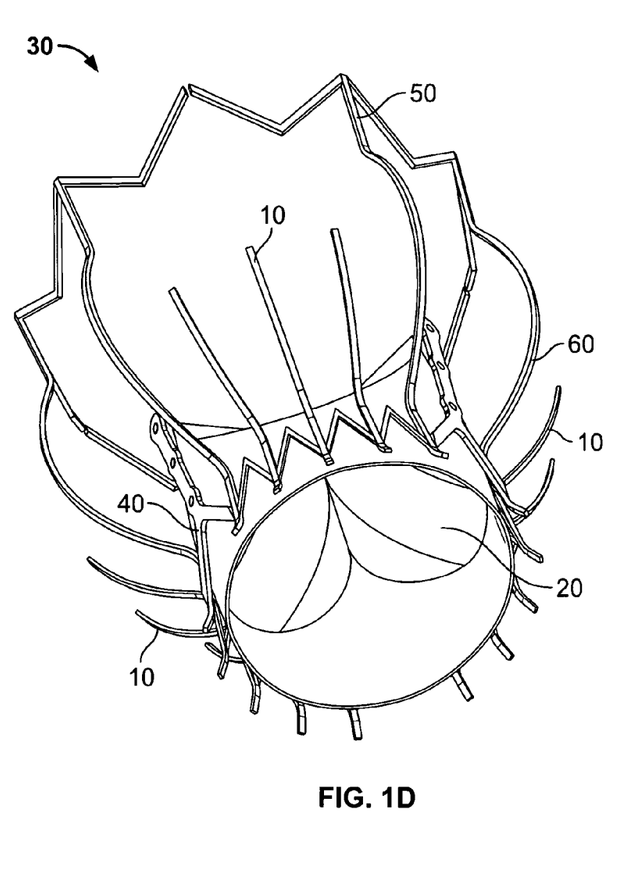
FIG. 1d shows the FIG. 1c structure from still another angle.
Figure 2A:
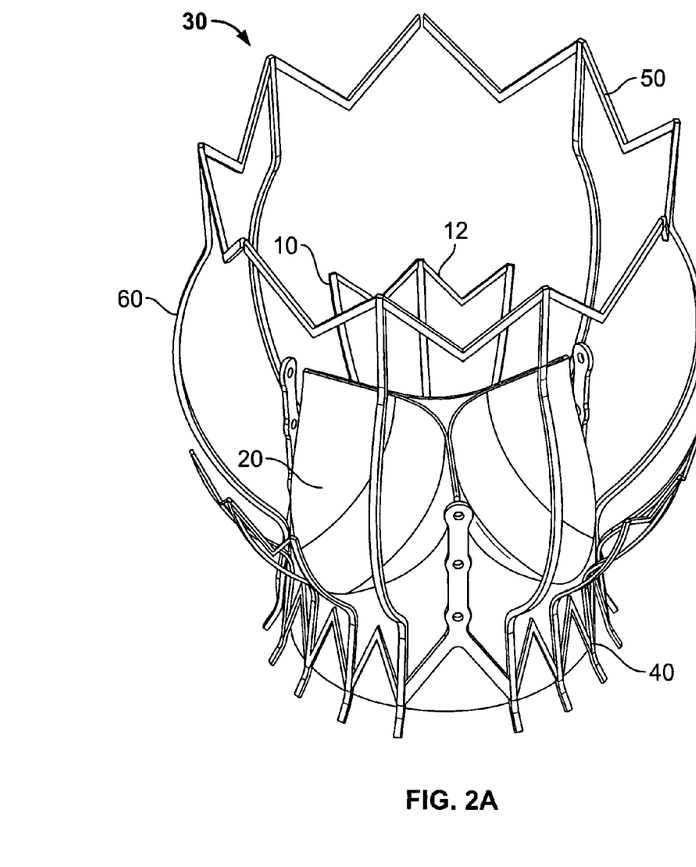
FIG. 2a is a view similar to FIG. 1a for another illustrative embodiment of a prosthetic heart valve in accordance with the invention.
Figure 2B:
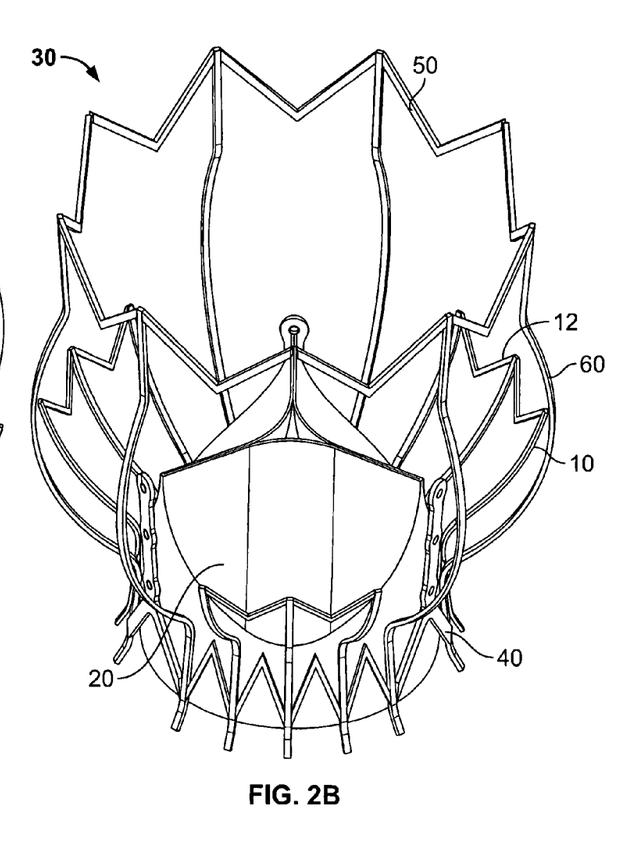
FIG. 2b shows the FIG. 2a structure from another angle.
Figure 2C:
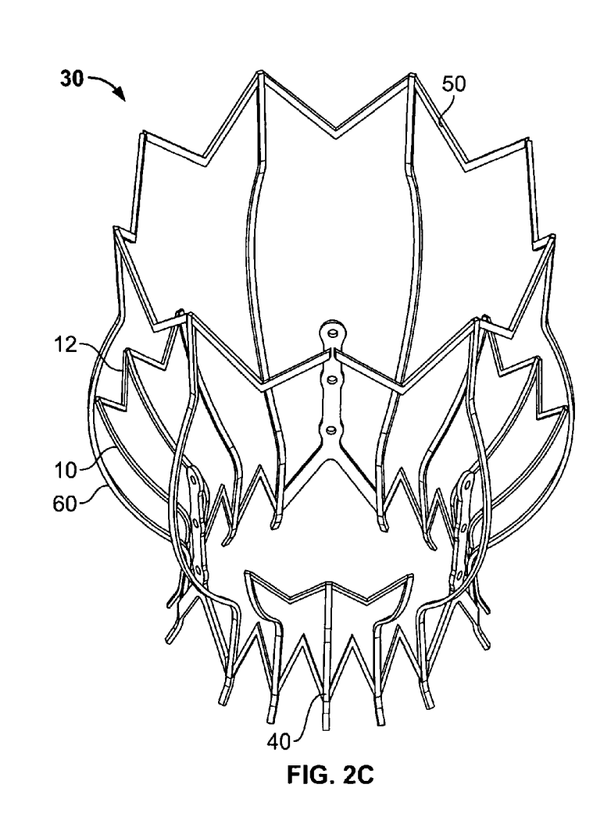
FIG. 2c is similar to FIG. 2b, but FIG. 2c shows only some of the structure that is shown in FIG. 2b.
Figure 2D:
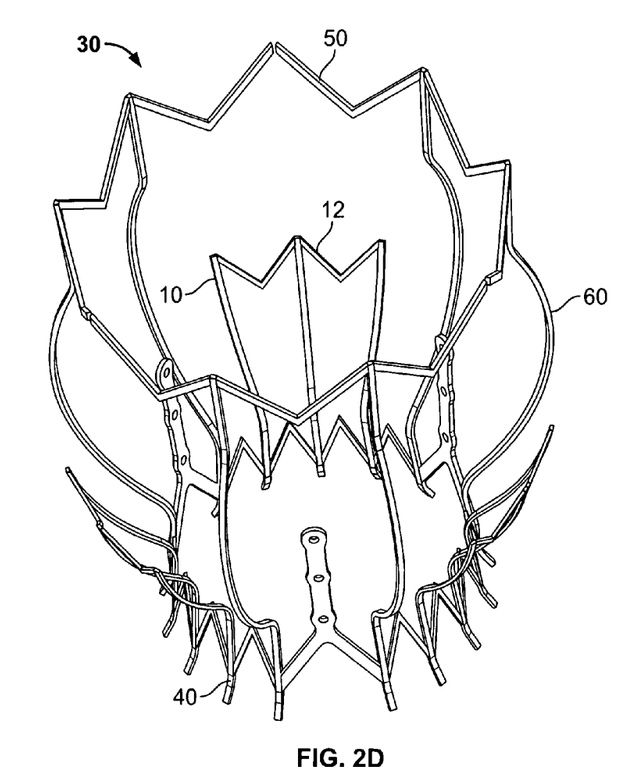
FIG. 2d shows the FIG. 2c structure from another angle.

FIGS. 2a-d are several views of another illustrative embodiment of the invention. Reference numbers are repeated from FIGS. 1a-d for features in FIGS. 2a-d that are similar to features in FIGS. 1a-d. FIGS. 2c and d omit depiction of the actual leaflet structure 20 to better reveal certain other features. The principal difference from FIGS. 1a-d is the inclusion in FIGS. 2a-d of collapsible/expandable interconnections 12 between the upper (cantilevered) ends of certain ones of fork-like fingers 10.

FIGS. 3a-d show several further alternative embodiments of the metal frame structure 10/40/50/60/etc. of valves in accordance with the invention. Again, reference numbers are repeated from earlier FIGS. for generally similar components. FIGS. 3a-d show each metal frame structure as though it has been cut along a longitudinal (vertical) axis and then laid out flat. In addition, FIGS. 3a-d show each metal structure in the approximate condition (especially from left to right as viewed in these FIGS.) that it has when annularly collapsed for delivery into a patient in reduced annular or circumferential size. Thus the serpentine or cellular structures (e.g., 40, 50, 12) that extend in the annular direction around the valve are somewhat collapsed or compressed in the left-right direction as viewed in FIGS. 3a-d. Annular portions 40 and 50 shown in FIGS. 3a-d are of a closed-cell design. This is an alternative embodiment to the undulating strut design shown in the earlier FIGS. (Again, it is emphasized that the structures shown in FIGS. 3a-d are not actually flat at any time during their use. They are always closed, annular structures. The flat depictions shown in FIGS. 3a-d are only employed for convenience herein.)

Figure 3A:
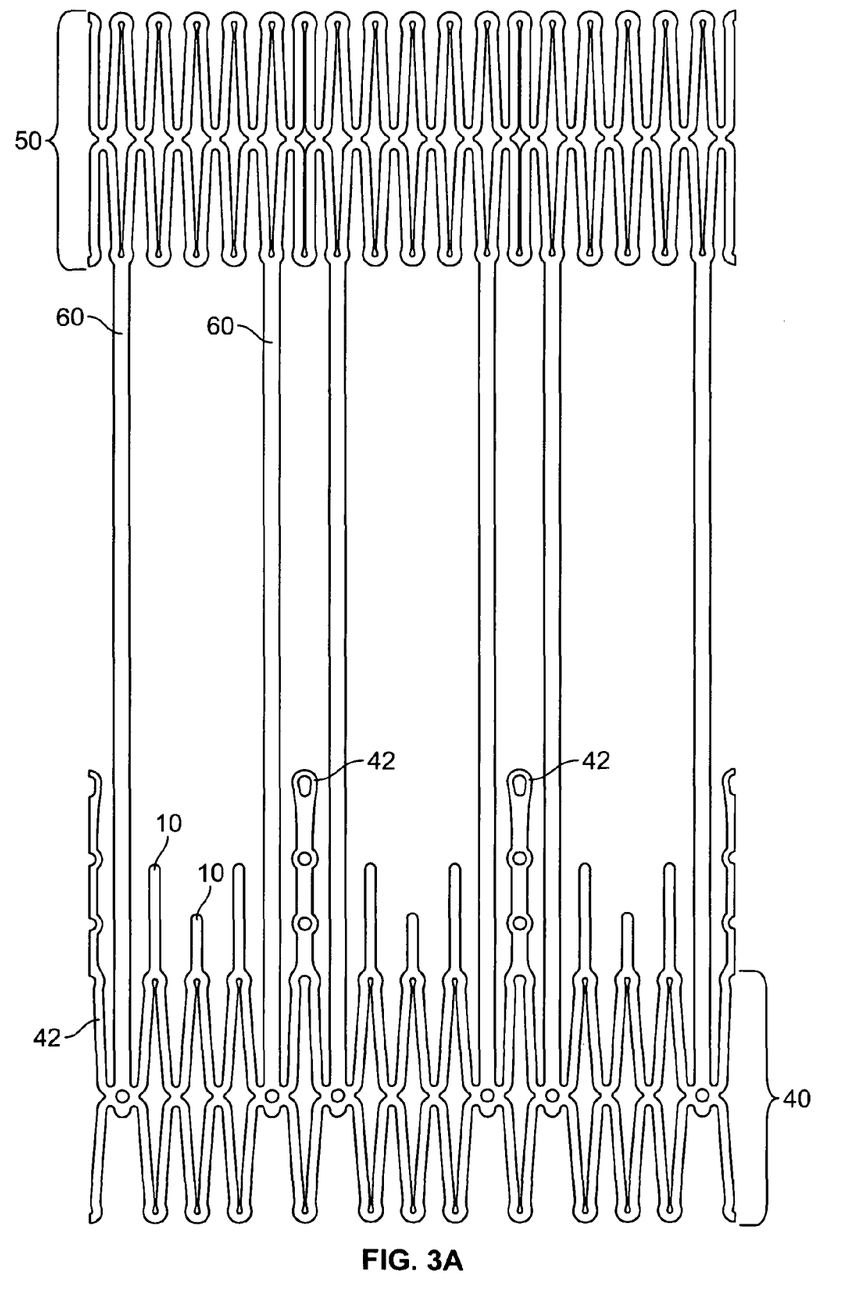
Figure 3B:
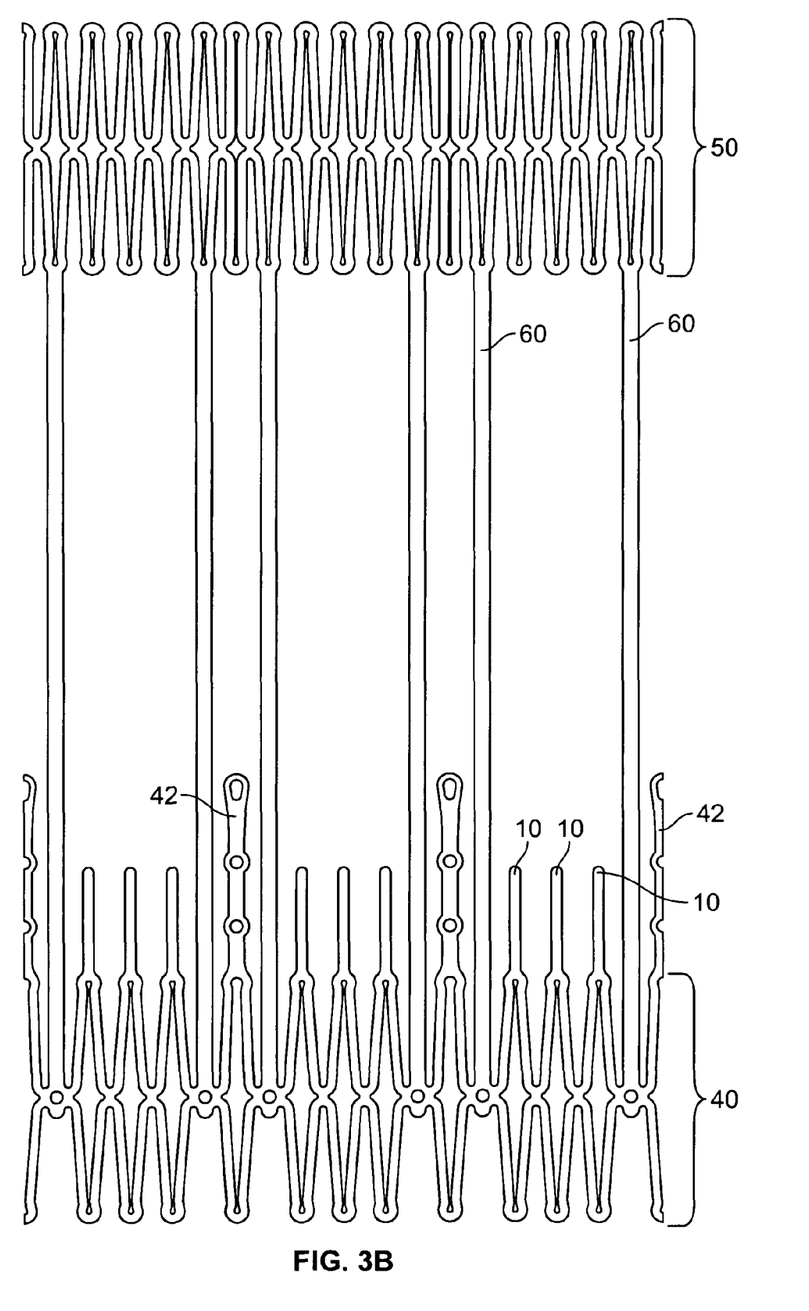
FIG. 3b is similar to FIG. 3a for another illustrative embodiment of the invention.

In FIG. 3a the upper ends of cantilevered fork-like fingers 10 are free (e.g., as in FIGS. 1a-d), but these fingers differ in length. In particular, fingers 10 are longer near (in the circumferential direction) each of the three circumferentially spaced commissure posts 42 of the valve, and shorter where farther (in the circumferential direction) from the commissure posts. Another way to state this is by saying that the fingers 10 that are circumferentially closer to commissure posts 42 extend farther in the distal or downstream direction than the fingers 10 that are circumferentially farther from the commissure posts. FIG. 3b shows fingers 10 all of the same length and with their upper ends free.

Figure 3C:
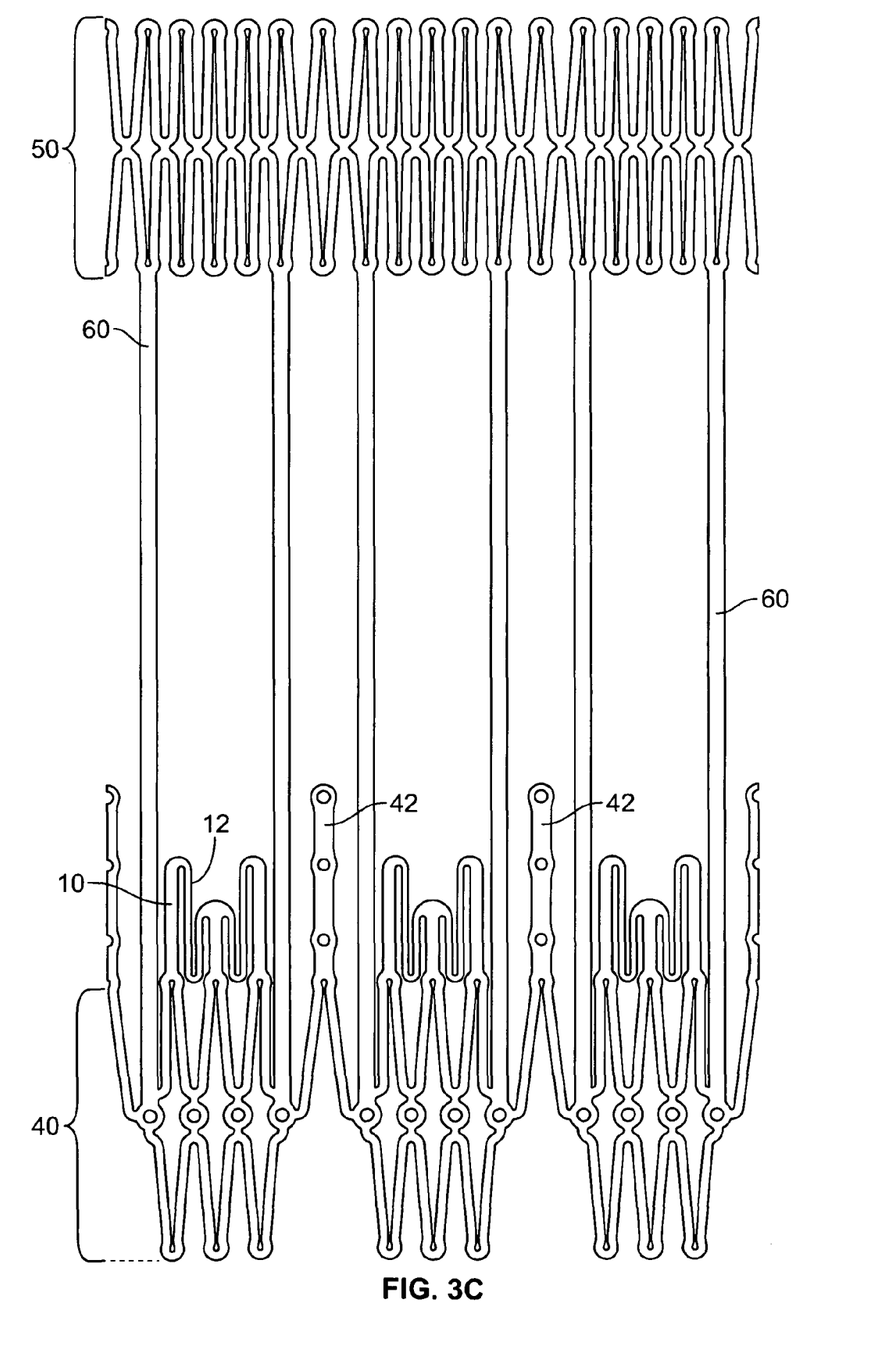
FIG. 3c is similar to FIG. 3b for yet another illustrative embodiment of the invention.

FIG. 3c shows an embodiment like FIG. 3a, but with the upper ends of the fingers 10 of different lengths linked by serpentine structures 12. Note that each serpentine structure 12 links only the fingers 10 in a set of such fingers that are located between two circumferentially adjacent ones of commissure posts 42. Thus the fingers 10 in such a set and the serpentine structure 12 linking those fingers collectively comprise a leaflet restraining structure that is cantilevered upwardly from annulus portion 40 of the prosthetic valve frame. This structure as a whole (i.e., the set of fingers 10 and the link 12) has a free end (i.e., its upper end, which in this case is defined by link 12).

Figure 3D:
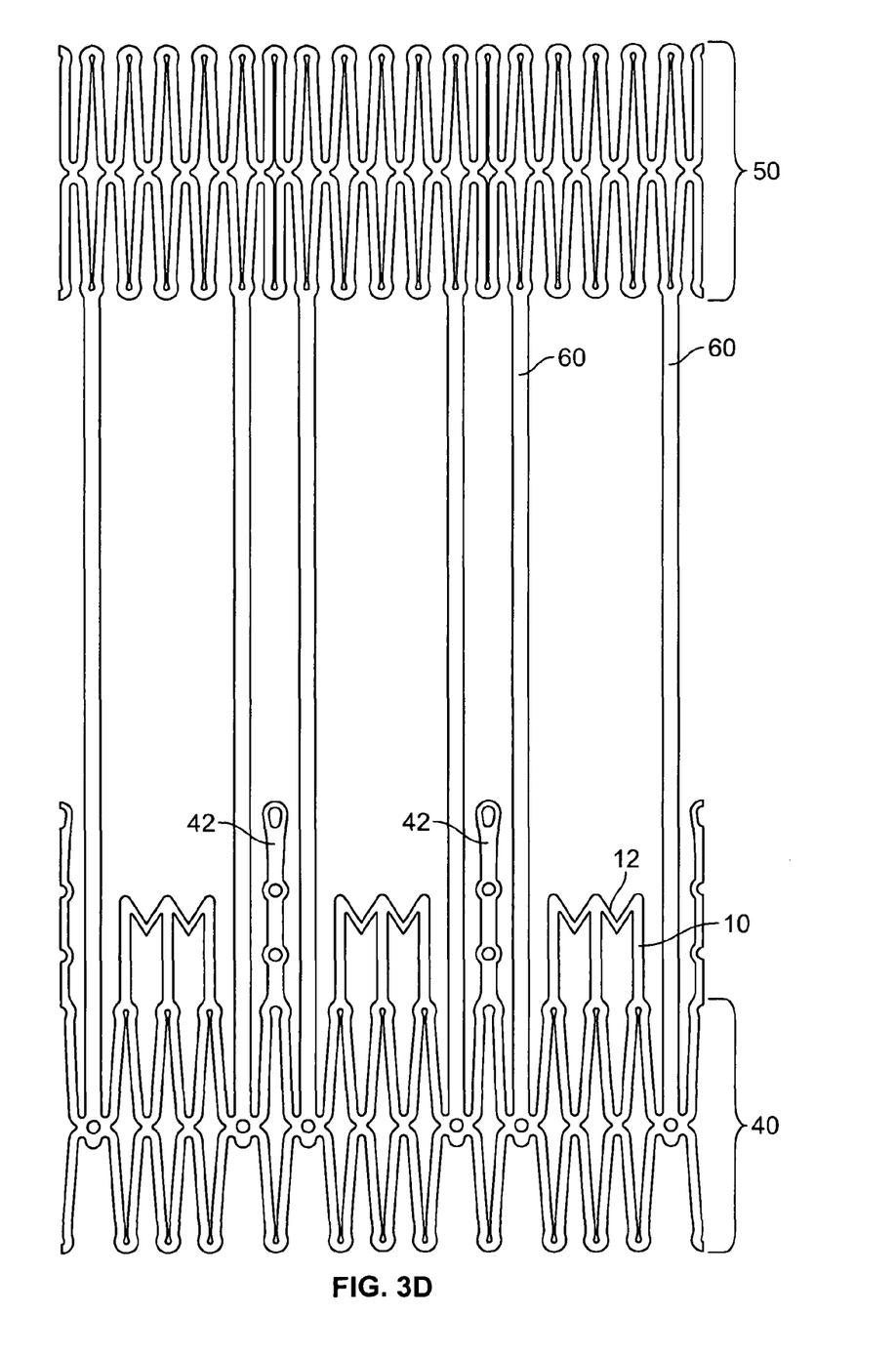
FIG. 3d is similar to FIG. 3c for still another illustrative embodiment of the invention.

FIG. 3d shows an embodiment like FIG. 3b, but with the upper ends of equal-length fingers 10 linked by serpentine structures 12. Once again, in FIG. 3d, each set of fingers 10 (between two circumferentially adjacent commissure posts) and the associated link 12 collectively constitute a leaflet restraining structure that is cantilevered up from annulus portion 40 to a free end (i.e., link 12). In embodiments without links 12, the fingers 10 themselves constitute the leaflet restraining structure of this invention.

Recapitulating and extending the above, the following are some of the important aspects of the invention.

Features 10 (possibly with links 12) are incorporated onto a collapsible valve frame and are designed specifically to hold the native calcified leaflet back (e.g., radially outwardly) and away from the replacement valve.

Features 10 (possibly with links 12) are preferably not tall enough such that they would obstruct the coronary artery ostia.

The cantilevered leaflet retention feature typically includes several elongated, curved, fork-like fingers 10 that can be free-standing or interconnected (e.g., as shown at 12) at the distal (downstream) end.

The fingers 10 are connected to the main stent frame at their proximal (upstream) end.

The fork-like fingers 10 may be curved radially outward, away from the replacement valve.

The fork-like fingers 10 (possibly with links 12) have adequate stiffness in the radial direction to hold the calcified native valve in an open (radially outward) position.

The fork-like fingers 10 (possibly with links 12) can be scalloped (e.g., FIG. 3a or 3c) or straight (e.g., FIG. 3b or 3d) at their distal end.

The fork-like fingers 10 (possibly with links 12) enhance anchoring of the prosthetic valve as a result of engaging the calcified leaflets.

While curved (radially) outward fork-like members 10 will do a good job keeping calcified leaflets out of the way, alternate designs can also be used, ranging from straight up fingers 10 to straight fingers inclined at an angle so that they are radially farther out at their free ends than where joined to annulus portion 40. Preferably, the prosthetic valve frame's geometry is designed to oppose the native leaflet once implanted and is capable of holding open, pushing outwards, engaging, and displacing the native leaflets in desired patterns to clear coronaries, and anchoring in the native leaflets. Many suitable geometries are capable of achieving these goals. The geometries can vary significantly and only some of the possible geometries are described herein.

Although the presently preferred stent structures (like 10/40/50/60) are self-expanding (i.e., elastically deformed), the present invention is equally applicable to balloon-expandable (i.e., plastically deformed) stents or a combination of self-expanding and balloon expandable (e.g., where arms like 10 are resiliently self-expanding, but the rest of the cage like 40/50/60 may be balloon-expanded). The balloon-expandable stents, which can be made of stainless steel, can be used with specifically designed balloons that have, for example, a bulbous midsection. The balloon-expendable stents can also be enlarged in two or more steps. A straight conventional balloon can be used first to anchor one or more stent structures of the valves. A second spherical balloon can then be used to specifically expand the other structure or structures such as fingers 10.

The structures like fingers 10 of this invention can also be designed to provide the following benefits. These structures preferably move the native calcified leaflets radially outwardly away from the new valve structure to avoid potential abrasion of the new valve tissue 20 against the calcified, diseased tissue. Use of this invention can provide more space for a bigger prosthetic valve and better hemodynamics. The structures like 10/12 of this invention can deform the diseased leaflets in such a way as to avoid potential coronary blockage (i.e. occlusion of the ostium of a coronary artery). The structures like 10/12 can be designed to also help with stability and anchoring of the prosthetic valve in the patient. Prior known collapsible prosthetic valves may include cages that are intended to push diseased leaflets out of the way. But these previously known structures do not attempt to control or preferentially displace the diseased leaflets in a specific configuration to provide the benefits described above for the present invention.

The attachment point of fingers 10 to the stent is described as being preferably at or near the proximal end of the prosthetic valve frame structure using the proximal end of the fingers. In another embodiment of the invention, the fingers can extend down from the distal end of stent (outflow side). Other combinations of attachment are also possible (e.g., stent inflow side and members 60 or stent outflow side and members 60).

The foregoing features can be incorporated on minimally invasive surgically implanted valves where resection of the native calcified leaflets has not been performed or is not possible.

An advantage of providing leaflet restraining structures 10/12 as structures that are cantilevered from other structure of the valve frame is that this facilitates giving the leaflet restraining structures various properties that can be relatively independent of the properties of other parts of the frame. For example, the extent to which leaflet restraining structures 10/12 incline or extend radially outwardly can be made to depend solely (or at least largely) on the design of those structures per se, and can be independent of the shape, location, etc., of other adjacent frame components such as links 60, commissure posts 42, aortic portion 50, etc. Similarly, those other portions of the valve can be designed to have properties that are independent of the properties of leaflet restraining structures 10/12. Examples of properties that can thus be designed independently for structures 10/12, on the one hand, and other portions of the frame, on the other hand, include (1) collapsed location (i.e., location during delivery), (2) re-expanded location (i.e., location when deployed and implanted in the patient), (3) size, (4) shape, (5) stiffness, (6) strength, (7) resilience, etc.

It will be understood that the foregoing is only illustrative of the principles of the invention, and that various modifications can be made by those skilled in the art without departing from the scope and spirit of the invention. For example, the number of leaflet restraining structures that are provided can be more or less than the number shown herein.

The invention claimed is:

1. A prosthetic heart valve comprising:
   an annular frame structure that is adapted for (1) delivery into a patient's native heart valve annulus in a circumferentially collapsed condition, and (2) circumferential reexpansion when in the annulus, the frame structure having a proximal end adjacent an annulus portion and a distal end, the proximal end having a first diameter and the distal end having a second diameter greater than the first diameter;
   a leaflet structure disposed in the frame structure; and
   at least two fingers spaced apart, each of the at least two fingers having a first end coupled to the annulus portion of the frame structure and being cantilevered from the annulus portion.

2. The prosthetic heart valve of claim 1, wherein the at least two fingers are equally spaced about a circumference of the frame.

3. The prosthetic heart valve of claim 1, wherein the at least two fingers are configured and arranged to align with native leaflets.

4. The prosthetic heart valve of claim 1, wherein each of the at least two fingers extend from the annulus portion toward the distal end.

5. The prosthetic heart valve of claim 1, wherein each of the at least two fingers include a free end disposed between the proximal end and the distal end of the frame.

6. The prosthetic heart valve of claim 1, wherein each of the at least two fingers are the same length.

7. The prosthetic heart valve of claim 1, wherein the at least two fingers comprise three fingers.

8. The prosthetic heart valve of claim 1, wherein the at least two fingers comprise three groupings of fingers, each grouping having multiple fingers.

9. The prosthetic heart valve of claim 8, wherein fingers of a grouping of fingers are coupled together via linking members.

10. The prosthetic heart valve of claim 1, wherein the at least two fingers are configured and arranged to push calcified native leaflets away from the frame.

11. A collapsible and expandable prosthetic heart valve comprising:
   an annular frame structure that is adapted for (1) delivery into a patient's native heart valve annulus in a circumferentially collapsed condition, and (2) circumferential reexpansion when in the annulus, the frame structure having a proximal end adjacent an annulus portion and a distal end, the proximal end having a first diameter and the distal end having a second diameter greater than the first diameter;
   a leaflet structure disposed in the frame structure; and
   at least two fingers circumferentially spaced about the annulus portion and coupled to the annulus portion, each of the at least two fingers being configured and arrange to move relative to the annular frame structure.

12. The prosthetic heart valve of claim 11, wherein the at least two fingers are equally spaced about a circumference of the frame.

13. The prosthetic heart valve of claim 11, wherein the at least two fingers are configured and arranged to align with native leaflets.

14. The prosthetic heart valve of claim 11, wherein each of the at least two fingers extend from the annulus portion toward the distal end.

15. The prosthetic heart valve of claim 11, wherein each of the at least two fingers include a free end disposed between the proximal end and the distal end of the frame.

16. The prosthetic heart valve of claim 11, wherein each of the at least two fingers are the same length.

17. The prosthetic heart valve of claim 11, wherein the at least two fingers comprise three fingers.

18. The prosthetic heart valve of claim 11, wherein the at least two fingers comprise three groupings of fingers, each grouping having multiple fingers.

19. The prosthetic heart valve of claim 18, wherein fingers of a grouping are coupled together via linking members.

20. The prosthetic heart valve of claim 11, wherein the at least two fingers are configured and arranged to push calcified native leaflets away from the frame.

* * * * *